United States Patent [19]

Hall et al.

[11] Patent Number: 5,100,907
[45] Date of Patent: Mar. 31, 1992

[54] HYDANTOIN ESTERS

[75] Inventors: Larry K. Hall, Cogan Station; Daniel W. Lemke, Jersey Shore, both of Pa.

[73] Assignee: Lonza, Inc., Fair Lawn, N.J.

[21] Appl. No.: 518,066

[22] Filed: May 2, 1990

[51] Int. Cl.$^5$ .............................................. A01N 43/50
[52] U.S. Cl. ................................. 514/385; 260/404.5; 260/404; 548/312; 514/727
[58] Field of Search .................... 260/404.5; 548/312; 514/385

[56] References Cited

U.S. PATENT DOCUMENTS 4,028,378 6/1977 MacFadyeh .................... 548/312

Primary Examiner—Jose G. Dees
Assistant Examiner—Deborah D. Carr
Attorney, Agent, or Firm—Darby & Darby

[57] ABSTRACT

Methylolated hydantoin fatty acid ester compounds having surfactant and biocidal preservative properties; compositions containing these ester compounds, e.g. solutions, emulsions and dispersions; and a method of killing or inhibiting the growth of microorganisms which includes contacting the microorganisms with such ester compounds.

10 Claims, 1 Drawing Sheet

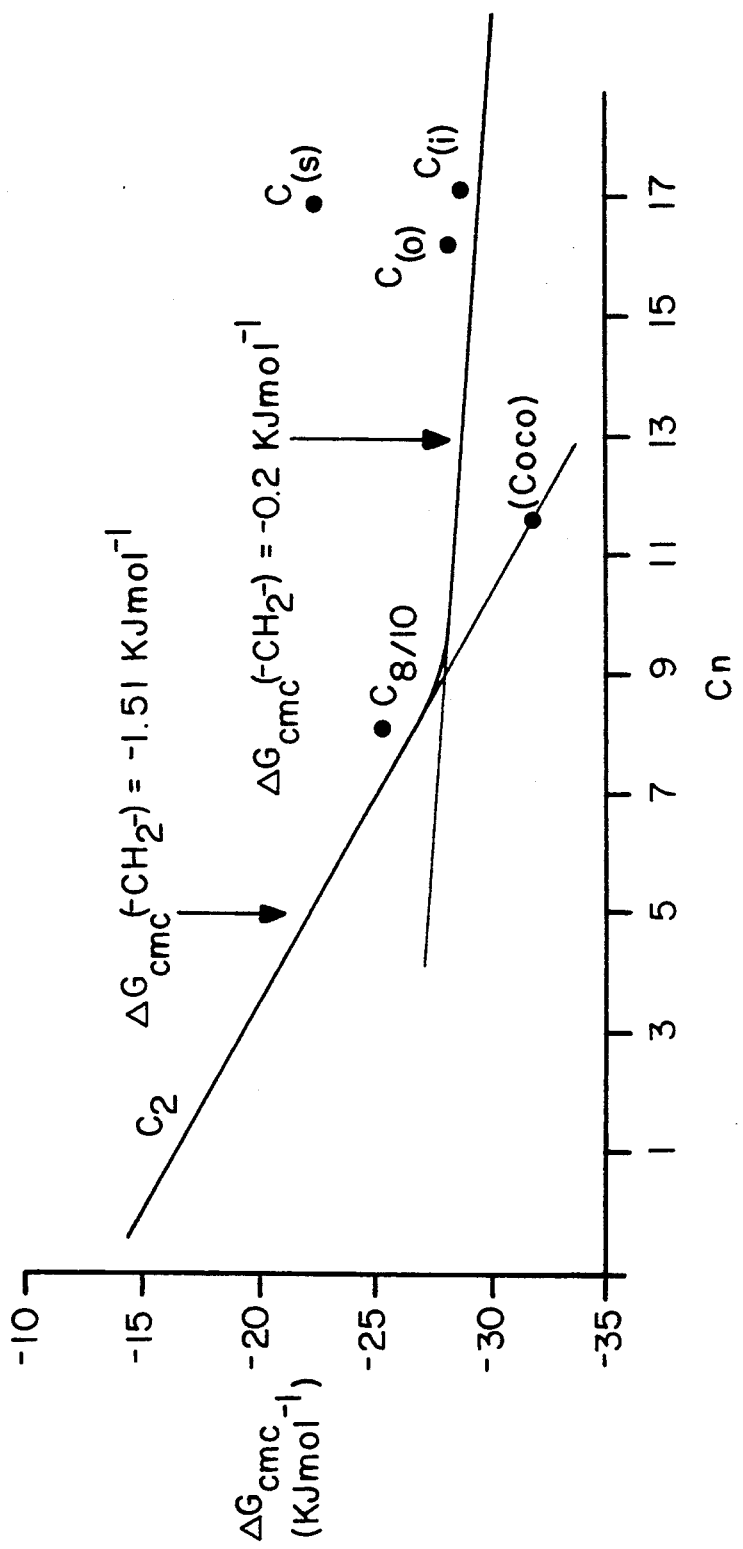

HYDANTOIN ESTERS

FIELD AND BACKGROUND OF THE INVENTION

This invention relates to hydantoin esters, and particularly methylolated hydantoin fatty acid ester compounds, having surfactant and biocidal properties, and usable in solutions, emulsions and dispersions, e.g. forming personal care, household, and industrial product, formulations.

All percentages (%), parts (pts) or proportions set forth herein are by weight unless specifically indicated otherwise.

Hydantoin, or 2,4-imidazolidinedione [i.e., 1,3-diazacyclopentane-2,4-dione], is a compound of the formula

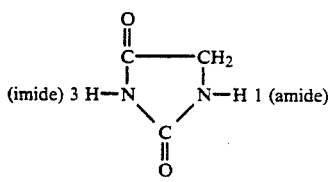

that has two active nuclear nitrogen atoms, i.e., an amide nitrogen at the 1-position and an imide nitrogen at the 3-position, per the bracketed naming system, both of which can be used to form derivatives.

One type of hydantoin compounds includes those based on the dimethyl derivative: dimethylhydantoin [i.e., 5,5-dimethyl-1,3-diazacyclopentane-2,4-dione], or simply DMH, of the formula

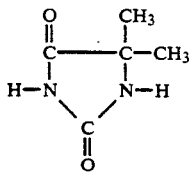

The corresponding methylolated hydantoins are biocides used in cosmetic preparations. They include the monomethylolated derivative: monomethylolated dimethylhydantoin [i.e., 1-hydroxymethyl-5,5-dimethyl-1,3-diazacyclopentane-2,4-dione], or simply MDMH, of the formula

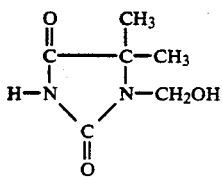

and the dimethylolated derivative: dimethylolated dimethylhydantoin [i.e., 1,3-dihydroxymethyl-5,5-dimethyl-1,3-diazacyclopentane-2,4-dione], or simply DMDMH, of the formula

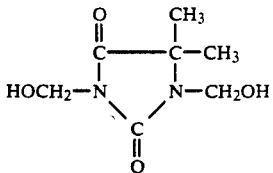

The dimethylolated hydantoin derivative DMDMH (iv) is effective as a formaldehyde donor at a minimum inhibitory concentration (MIC) of 0.1%. The monomethylolated hydantoin derivative MDMH (iii) is effective at 0.2% MIC, as its biocidal activity is half that of the dimethylolated derivative DMDMH (iv), since it can donate only half as much formaldehyde (traceable to the hydroxymethyl group) per molecule.

Other known hydantoin derivatives are the polyethoxylated hydantoin esters: di(polyethoxylated) dimethylhydantoin esters [i.e., 1,3-di(polyethylene oxide)-5,5-dimethyl-1,3-diazacyclopentane-2,4-diones), or simply DEOXDMH esters, of the formula

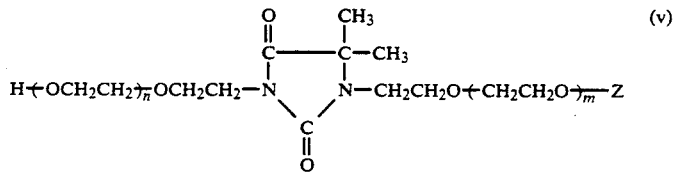

wherein m and n are 5-15, Z is H or —C(O)R, and R is the aliphatic group of a fatty acid radical. The DEOXDMH esters (v) are emulsifiers, e.g. used in the textile industry for fiber finishing applications, and are not biocidal formaldehyde donors.

Aside from the MDMH (iii) and DMDMH (iv) biocides, and DEOXDMH ester (v) emulsifiers, the literature only appears to disclose hydantoin esters of radically different structure, used as ultraviolet (UV) absorbers or for medical or other remote purposes. As to lipophilic molecules having biocidal activity, certain fatty acids are known to have such activity in addition to surfactancy, but these do not involve hydantoin based molecules. Those instances of esters that perform as a bifunctional surfactant/biocide are mostly concerned with glycerol esters.

Common cosmetic preservatives are DMDMH (iv), Quaternium 15 (Dowicil 200, a trademark of Dow Chemical Co.), imidazolidinyl urea (Germall 115, a trademark of Sutton Laboratories), parabens [alkylhydroxybenzoates], phenols [alkylphenol], phenoxyethanol, isothiazolinones, fatty acids, monoglycerol esters, formaldehyde and 2-bromo-2-nitropropane-1,3-diol.

Formaldehyde donor biocides are effective against bacteria, and to a lesser extent against molds or yeast, in cosmetic or health care preparations, e.g. shampoos, hair rinses, creams, soft soaps, etc. In such preparations, surface active biocides are effective against molds and yeast, and to a lesser extent against bacteria, their antimicrobial activity against these organisms tending to increase markedly with increase in their lipophilic, e.g. alkyl, chain, up to a specific length.

Generally, to provide the cosmetic formulation with a broad spectrum preservative system against all organisms, i.e., of the bacteria, mold, and yeast, groups, a multiple number of biocides, each specifically effective against a given group, are combined.

U.S. Pat. No. 4,844,891 teaches a synergistic combination of biocides as a broad spectrum preservative system for a wide variety of product formulations.

It would be desirable to have a compound that combines the attributes of an effective biocide and a surface active agent in one molecule, forming a stable product, e.g. usable in cosmetic formulations, that can be synthesized in quantitative yield by a simple process, and that reduces the inventory that would otherwise require two or more compounds for such purposes.

SUMMARY OF THE INVENTION

This invention achieves the above desire in providing methylolated monohydroxyethyl-dimethylhydantoin fatty acid esters combining the attributes of both an effective biocide and a surface active agent in one molecule, that constitute stable products, e.g. usable in personal care, household, and industrial, product formulations, that can be made quantitatively by a simple process, and that reduce the inventory otherwise requiring a combination of compounds for such purposes.

These distinct dual-performance surfactant/preservative hydantoin esters are synthesized by a process of minimum steps from an available hydantoin based starting material, and constitute hydantoin compounds that have both a surfactant moiety and a biocidal moiety. They have significant physical properties, including surfactancy, e.g. significant critical micelle concentration (cmc), Gibbs' Free Energy of Micellation ($\Delta G°_{cmc}$), and hydrophilic-lipophilic balance (HBL), values, plus significant biological activity, i.e., biocidal properties, e.g. against molds (fungi), and gram-positive and gram-negative bacteria.

Such dual properties permit preparation of various solutions, emulsions and dispersions of these hydantoin esters that are useful, for example by way of incorporation in conventional substances or materials such as personal care, e.g. cosmetic, product formulations, household, e.g. detergent, product formulations, industrial product formulations, e.g. latex dispersions, industrial slurries, etc. Their performance compares favorably with structurally similar known surfactants, i.e., fatty acid esters, and separately with structurally similar known biocides, i.e., methylolated hydantoins such as MDMH (iii) and DMDMH (iv).

BRIEF DESCRIPTION OF THE DRAWING

The drawing FIGURE is a graph showing the relation between change in Gibbs' Free Energy of Micellation ($\Delta G°_{cmc}$) and lipophilic chain length of typical esters of the invention.

DESCRIPTION OF THE INVENTION

Generally, the invention comprises hydantoin fatty acid esters of the formula

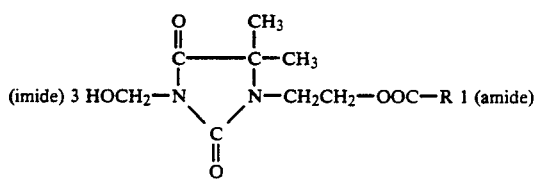

wherein R—COO— is a fatty acid moiety. Using the hydantoin (i) numbering system noted above, these esters have a 1-position amide nitrogen atom and a 3-position imide nitrogen atom.

These methylolated hydantoin fatty acid esters may be termed methylolated monohydroxyethyl dimethylhydantoin esters, or 3-hydroxymethyl-5,5-dimethylhydantoin-1-yl ethyl esters of fatty acids [i.e., 3-hydroxymethyl-5,5-dimethyl-1,3-diazacyclopentane-2,4-dione-1-yl ethyl esters of fatty acids], or simply methylolated MHEDMH esters (I).

Their fatty acid moiety generally has 2–20, especially 2–18, and more especially 8–18, carbon atoms. Typically, this moiety is an acetic, caprylic, capric, lauric, coconut, oleic, isostearic or stearic moiety. Depending on the fatty acid material used to make the ester (I), the product may be in the form of a mixture of esters of different fatty acid moieties, such as in the case of a caprylic acid/capric acid starting material or $C_{8/10}$ acid (i.e., aliphatic carboxylic or fatty acid) mixture.

As used herein, a "$C_{8/10}$" acid is meant to be interchangeable with a caprylic acid/capric acid mixture or blend, especially an approximately 1:1 blend of these two fatty acids that have 8 and 10 carbon atoms, respectively, in their molecules.

The aliphatic radical R of the R—COO— moiety may be a straight or branched chain saturated or unsaturated radical such as alkyl or alkenyl, and will have one less carbon atom in the lipophilic chain that the corresponding fatty acid used to form the ester (I); e.g. R may have 1–19, especially 1–17, and more especially 7–17, carbon atoms.

Typical esters (I) include:

the 2-(3-hydroxymethyl-5,5-dimethyl-1,3-diazacyclopentane-2,4-dion-1-yl)-ethyl ester of acetic acid;

a mixture of the 2-(3-hydroxymethyl-5,5-dimethyl-1,3-diazacyclopentane-2,4-dion-1-yl)-ethyl esters of caprylic acid and capric acid;

the 2-(3-hydroxymethyl-5,5-dimethyl-1,3-diazacyclopentane-2,4-dion-1-yl)-ethyl ester of lauric acid;

the 2-(3-hydroxymethyl-5,5-dimethyl-1,3-diazacyclopentane-2,4-dion-1-yl)-ethyl ester of coconut fatty acid;

the 2-(3-hydroxymethyl-5,5-dimethyl-1,3-diazacyclopentane-2,4-dion-1-yl)-ethyl ester of oleic acid;

the 2-(3-hydroxymethyl-5,5-dimethyl-1,3-diazacyclopentane-2,4-dion-1-yl)-ethyl ester of isostearic acid; and the 2-(3-hydroxymethyl-5,5-dimethyl-1,3-diazacyclopentane-2,4-dion-1-yl)-ethyl ester of stearic acid.

The esters (I) may be in the form of a mixture with a liquid vehicle such as water, an alcohol and/or mineral oil.

The esters (I) are readily made from the corresponding nonmethylolated hydantoin fatty acid esters of the formula

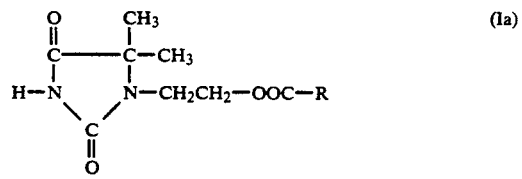

wherein R—COO— is a fatty acid moiety as defined above.

These non-methylolated esters may be termed monohydroxyethyl dimethylhydantoin esters, or 5,5-dimethylhydantoin-1-yl ethyl esters of fatty acids [i.e., 5,5-dimethyl-1,3-diazacyclopentane-2,4-dione-1-yl ethyl esters of fatty acids], or simply MHEDMH esters (Ia).

The process for preparing the hydantoin esters (Ia) and (I) is carried out according to the following reaction schemes:

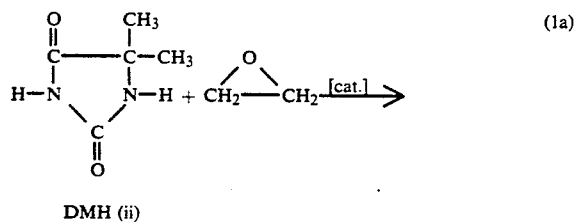

DMH (ii)

MHEDMH (vi)

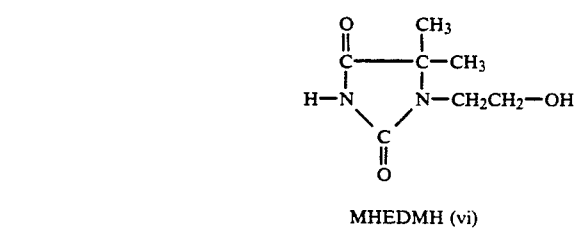

MHEDMH (vi)

MHEDMH Ester (Ia)

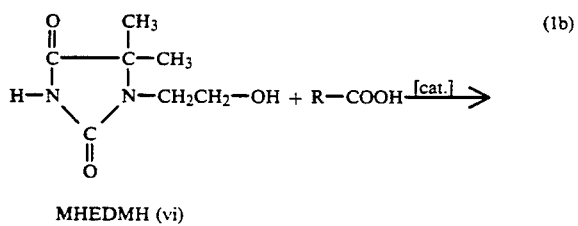

MHEDMH Ester (Ia)

Methylolated MHEDMH Ester (I)

Thus, to make the non-methylolated hydantoin fatty acid ester, or MHEDMH ester (Ia), 5,5-dimethylhydantoin, or DMH (ii) [$C_5H_8O_2N_2 = 128$ mol. wt.], is reacted with ethylene oxide in a first step per reaction scheme (1a), e.g. in the presence of a catalyst such as sodium hydroxide, to form monohydroxyethyl dimethylhydantoin, or 1-(2-hydroxyethyl)-5,5-dimethylhydantoin [i.e., 1-(2-hydroxyethyl)-5,5-dimethyl-1,3-diazacyclopen-tane-2,4-dione], or MHEDMH (vi) [$C_7H_{12}O_3N_2 = 172$ mol. wt.].

In a second step per reaction scheme (1b), a fatty acid of the formula RCOOH whose RCOO— moiety is as defined above, is esterified, e.g. in the presence of a catalyst such as hypophosphorous acid [$HP(OH)_2$], with the 1-(2-hydroxyethyl)-5,5-dimethylhydantoin (vi) recovered from the first step reaction mixture, to form the corresponding 2-(5,5-dimethylhydantoin-1-yl)-ethyl fatty acid ester, or MHEDMH ester (Ia).

In the first step per reaction scheme (1a), the reaction may also produce a minor amount of dihydroxyethyl dimethylhydantoin, or 1,3-di(2-hydroxyethyl)-5,5-dimethylhydantoin [i.e., 1,3-di(2-hydroxyethyl)-5,5-dimethyl-1,3-diazacyclopentane-2,4-dione], or DHEDMH (vii) [$C_9H_{16}O_4N_2 = 216$ mol. wt.] of the formula

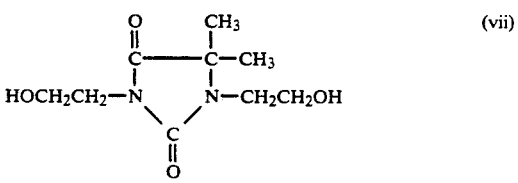

In turn, to make the methylolated hydantoin fatty acid ester, or methylolated MHEDMH ester (I), the ester (Ia) is methylolated with formaldehyde in a third step per reaction scheme (1c), e.g. in the presence of a catalyst such as sodium bicarbonate, to form the corresponding 2-(3-hydroxymethyl-5,5-dimethylhydantoin-1-yl)-ethyl fatty acid ester, or methylolated MHEDMH ester (I).

In producing the ester (I), the ester (Ia) formed in the esterifying step may be recovered from the reaction mixture and then methylolated. However, it may be directly methylolated to the ester (I) without intervening recovery from the esterifying step reaction mixture, thus simplifying the production procedure.

All esterification and methylolation reactions proceeded smoothly and were quantitative in making the esters (Ia) and (I).

The non-methylolated ester (Ia) is both the production process precursor of the methylolated ester (I), and its immediate formaldehyde release by-product when the ester (I) is demethylolated per its biocidal action as formaldehyde donor.

Typical aliphatic carboxylic (alkanoic or alkenoic) acids used to make these esters are acetic acid, a caprylic/capric acid blend or mixture (e.g. 1:1), coconut fatty acid, lauric acid (e.g. 98% pure), oleic acid, isostearic acid, and stearic acid.

The selective varying of the alkyl or alkenyl chain length and substitution, i.e., branching and unsaturation, that is possible, permits wide flexibility to "tailor fit" the solvent characteristics of the ester to that of the intended formulation, e.g. to provide an effective biocide with selective surface active properties, while reducing the inventory needed, e.g. for a cosmetics manufacturer, because the attributes of two otherwise needed raw materials, i.e., a biocide (preservative) and a surface active agent (emulsifier) are combined in the one ester.

Table 1 summarizes fatty aid chain length percent distribution, and number ratio (#C:# unsat.) of carbon atoms to double bonds (instances of ethylenic unsaturation), as determined by gas chromatography (GC), of typical fatty acids used herein.

TABLE 1

| Fatty Acid Percent Distribution as Determined By GC | | | | | | |
|---|---|---|---|---|---|---|
| # C:# unsat. | Acetic | C$_{8/10}$ | Lauric | Coconut | Oleic | Stearic |
| 6:0 | — | 1.4 | — | 0.4 | — | — |
| 8:0 | — | 46.8 | — | 5.8 | — | — |
| 10:0 | — | 51.1 | 1 | 5.8 | — | — |
| 12:0 | — | 0.7 | 98 | 52.3 | 0.2 | — |
| 14:0 | — | — | 1 | 22.5 | 2.6 | — |
| 14:1 | — | — | — | — | 1.7 | — |
| 16:0 | — | — | — | 8.4 | 4.9 | 4.4 |
| 16:1 | — | — | — | — | 7.4 | — |
| 18:0 | — | — | — | 1.5 | 1.2 | 94.9 |
| 18:1 | — | — | — | 2.5 | 74.4 | — |
| 18:2 | — | — | — | 0.5 | 5.2 | — |
| 18:3 | — | — | — | — | 0.8 | — |
| 20:0 | — | — | — | — | — | 0.7 |

Note: No standards were available to quantitate the percent fatty acid distribution of the isostearic acid used.

It will be noted that these aliphatic acids include instances of dienyl and trienyl unsaturation as well as mono-enyl (ethenylene) unsaturation. In Table 1, the C$_{8/10}$ acid is a 1:1 caprylic/capric acid blend, and the lauric acid is +98% pure.

The acid moiety generally ranges from 2–20, especially 2–18, carbon atoms as shown in Table 1, to provide a broad range of lipophilic aliphatic chain lengths R attached to the carbonyloxy (—COO—) group of the esters (I) for combined biocidal activity and surfactancy in one molecule at selectively maximized dual functioning in terms of R chain length and makeup. The oleate and isostearate esters typify the effect of unsaturation and methyl branching on preservative/surfactant performance.

The structure of each pertinent produce formed per reaction schemes (1a) to (1c) was evidenced by the following analyses:

DMH (ii): Proton NMR, IR, and GC retention time.
MHEDMH (vi): Proton NMR, IR, OH value, and GC retention time.
MHEDMH Ester (Ia): IR, OH value, AV value (acid value), and performance.
Methylolated MHEDMH Ester (I): IR, FF (free formaldehyde), and TF (total formaldehyde) level.

All the esters (I) release formaldehyde quantitatively, and thus serve as effective preservatives. The laurate, cocoate, oleate, and isostearate esters (I) exhibit particularly favorable surface active properties.

It is especially surprisingly that the esters (I) act as self-preserving surfactants, that do not require the addition of a microbiological preservative in order to prevent biodeterioration, and that the necessary biocidal activity is achieved without problems, despite the inclusion of a fatty acid surfactant moiety on the molecule. It was to be expected that this surfactant moiety would adversely affect the hydroxymethyl biocidal moiety because the introduction of a long hydrocarbon chain would be considered to interfere with the biocidal properties of the molecule. The modification of existing molecular structures often negates previously identified performance properties.

Due to their physical, especially surface active, properties, the esters (I) may be included compatibly in the usual amounts for such purposes, in conventional substances or materials such as product formulations where inhibiting the growth of microorganism is necessary, for providing at the same time enhanced biocidal action, due to the formaldehyde donor properties of the esters (I).

These product formulations include, for instance, personal care product formulations, e.g. cosmetics, shampoos, hair rinses, creams, lotions, soft soaps, and the like; household product formulations, e.g. laundry detergents, hard surface cleaners, fabric softeners, and the like; industrial product formulations, e.g. latex dispersions, paints, pigment dispersions, and industrial slurries in general, as for use in treating wood, textiles, leather, rope, paper pulp, fuel oil, metal working or drilling fluids, etc.

The amount of the ester (I) used, of course, depends on the particular application, but will be least be sufficient to provide the biocidal effect desired, and will also be sufficient to provide the contemplated degree of surfactant effect desired. The amount of the ester (I) present will generally be about 0.1–10%, preferably about 0.5–5%, e.g. about 1.5–3%, by weight of the total composition of the product formulation.

Conveniently, the surfactant effect of the ester (I) may be supplemented by inclusion of compatible known surfactants such as those used to attain specific effects, e.g. in particular personal care and household product formulations. As the shelf life of these formulations often depends on their resistance to microbial spoilage, the amount of the ester (I) included must be sufficient to provide a biocidally preservative effect.

Thus, in formulating the particular composition, the amount or concentration of the ester (I) will be selected to achieve a biocidally preservative effect against the specific microorganisms which are to be inhibited. This minimum inhibitory concentration (MIC) can be readily determined by simple laboratory experimentation using standardized testing techniques.

The incorporation of the esters (I) into these product compositions is done in accordance with standard practices. The resulting product formulations are desirably not odoriferous nor irritating or toxic when applied to the skin.

Typical esters (I) have been found to be effective to inhibit the growth of such molds (fungi) and bacteria as: *Aspergillus niger* (mold); *Staphylococcus aureus* (gram-positive bacteria); *Escherichia coli* and *Pseudomonas aeruginosa* (gram-negative bacteria); and the like.

Thus, the invention contemplates compositions of the above kind comprising a carrier such as a liquid material of the aforesaid type, e.g. a cosmetic, in the form of a solution, emulsion or dispersion, and a biocidally effective amount of the ester (I). The invention also contemplates a method of biocidally controlling, e.g. killing or inhibiting the growth of, microorganisms, such as molds (fungi), gram-positive bacteria, and/or gram negative bacteria, comprising contacting the microorganisms with a biocidally effective amount of the ester (I).

EXAMPLES

The following examples are merely illustrative of preferred embodiments of the invention. Many variations thereon may be made without departing from the spirit of the invention, as will be evident to those skilled in the art, and such variations are intended to come within the scope of what is claimed.

EXAMPLE A

Preparation of MHEDMH (vi) from DMH (ii)
[Reaction Scheme (1a)]

Monohydroxyethyl dimethylhydantoin [i.e., 1-hydroxyethyl-5,5-dimethyl-1,3-diazacyclopentane-2,4- dione], or MHEDMH (vi), was prepared from dimethylhydantoin [i.e., 5,5-dimethyl-1,3-diazacyclopentane-2,4-dione], or DMH (ii), as follows:

DMH (500 g, 3.902 mols), sodium hydroxide (1.5 g, 50% aq.), and water (300 g, distilled), were combined in a 2-liter (Series 4501 Parr) autoclave. The reaction apparatus was sealed, purged with nitrogen gas, and heated to 95° C. Ethylene oxide (188 g, 4.268 mols) was then added at 95° C. and reacted for two hours. The reactor was allowed to cool to room temperature and the contents were poured into a 2-liter, 4-neck, flask. The major amount of water was then stripped at 105° C. and atmospheric pressure. The remainder of the water, trace glycerol and by-products of the hydrolysis of ethylene oxide, was stripped at 140° C. and at a vacuum below 1 mm Hg. The final product was then poured onto an aluminum foil and allowed to crystallize.

The product appeared as a white crystalline solid with a melting point (mp) of 72.5°–73.5° C.

Gas chromatograph analysis showed it to contain DMH (ii) (0.93%), MHEDMH (vi) (77.25%), and dihydroxyethyl dimethylhydantoin (21.8%) [i.e., 1,3-dihydroxyethyl-5,5-dimethyl-1,3-diazacyclopentane-2,4-dione], or DHEDMH (vii).

The yield of 1-hydroxyethyl-5,5-dimethyl-1,3-diazacyclopentane-2,4-dione [MHEDMH (vi)] was 557 g (83% of the theoretical yield of 605 g).

Proton NMR (ref., TMS): $CH_3$, 1.44 ppm (s, 6H); $CH_2$, 3.73 ppm (t, 4H, 5.4 Hz); OH, 3.80 ppm (s, 1H); and NH, 7.23 ppm (s, 1H). The MHEDMH (vi) was twice recrystallized in a mixture of the cosolvents, dichloroethane (95 vol. %) and xylene (5 vol. %), prior to analyzing the NMR.

EXAMPLE B

Preparation of MHEDMH Coconut Fatty Acid Ester (Ia) from MHEDMH (vi) [Reaction Scheme (1b)]

The non-methylolated monohydroxyethyl dimethylhydantoin ester of coconut fatty acid (cocoate), or 5,5-dimethylhydantoin-1-yl-ethyl ester of coconut fatty acid [i.e., 5,5-dimethyl-1,3-diazacyclopentane-2,4-dione-1-yl-ethyl ester of coconut fatty acid], or MHEDMH cocoate (Ia), was prepared from MHEDMH (vi) of Example A, as follows:

MHEDMH (1377.4 g, 8.00 mols), coconut fatty acid (2012.0 g, 10.0 mols), and hypochlorous acid (3.79 g), were added to a 5-liter, 4 neck, flask. The flask was fitted with a mechanical stirrer, temperature control, nitrogen sparge tube, six inch packed column, condenser and receiver, and vacuum capabilities to 1 mm Hg. With the nitrogen sparge set on low, the batch was slowly heated at 230° C. at atmospheric pressure and at such a rate as to maintain a column head temperature of less than 105° C. After 5 hours, the batch was at 230° C., about 150 ml of water had been collected, and the material had an acid value (AV) of 39.

A second charge of hypophosphorous acid (2.44 g) was then added and the batch was reacted for an additional 8 hours at 230° C. After a total reaction time of 14 hours, the acid value was 29. At this point, a vacuum was slowly applied to the batch and the nitrogen sparge was left on low. The excess fatty acid was stripped off at 4 mm Hg. When the column head temperature had dropped below 100° C. and no liquid condensate was observed in the condenser, the batch was cooled to room temperature.

Final analysis showed the material [ester (Ia)] to have a mp of 57.3° C., color (Lovibond) of 9 yellow/4 red, acid value (AV) of 5.5, hydroxyl value (OH) of 5.6, and saponification value of 134.

The yield of 5,5-dimethyl-1,3-diazacyclopentane-2,4-dione-1-yl-ethyl ester of coconut fatty acid [ester (Ia)] was 2,933 g (91% of the theoretical yield of 3,216 g).

Infra Red (neat) showed: 3290 (br), 1785 (sharp), 1740 (sharp), 1710 (br), and 1160 (sharp).

The same procedure was used to prepare the esters (Ia) of the other fatty acids listed in Table 1, and of isostearic acid.

These typical precursor esters (Ia) are:

the 2-(5,5-dimethyl-1,3-diazacyclopentane-2,4-dion-1-yl)-ethyl ester of acetic acid;

a mixture of the 2-(5,5-dimethyl-1,3-diazacyclopentane-2,4-dion-1-yl)-ethyl esters of caprylic acid and capric acid;

the 2-(5,5-dimethyl-1,3-diazacyclopentane-2,4-dion-1-yl)-ethyl ester of lauric acid;

the 2-(5,5-dimethyl-1,3-diazacyclopentane-2,4-dion-1-yl)ethyl ester of coconut fatty acid;

the 2-(5,5-dimethyl-1,3-diazacyclopentane-2,4-dion-1-yl)-ethyl ester of oleic acid;

the 2-(5,5-dimethyl-1,3-diazacyclopentane-2,4-dion-1-yl)-ethyl ester of isostearic acid; and 2-(5,5-dimethyl-1,3-diazacyclopentane-2,4-dion-1-yl)-ethyl ester of stearic acid.

Table 2 shows some physical properties of these esters (Ia).

TABLE 2

| Physical Properties of Non-Methylolated MHEDMH Esters (Ia) | | | | |
|---|---|---|---|---|
| Acid Used To Prepare Ester | Appearance at 25° C. | Melting Point °C. | Acid Value AV | Hydroxyl Value OH |
| Acetic | White Crystals | 81–82.5 | 1.7 | 19.7 |
| $C_{8/10}$ | White Solid | 89.5–40 | 1.2 | 9.7 |
| Lauric | White Solid | 73–74.5 | 0.2 | 0.2 |
| Coconut | White Solid | 57.3 | 5.5 | 5.6 |
| Oleic | Off White Solid | 30.0 | 4.7 | 7.6 |
| Isostearic | Viscous Liquid | — | 5.0 | 9.2 |
| Stearic | White Solid | 87.4 | 4.3 | 8.6 |

EXAMPLE C

Preparation of Methylolated MHEDMH Coconut Fatty Acid Ester (I) from Corresponding Non-Methylolated MHEDMH Ester (Ia) [Reaction Scheme (1c)]

The methylolated monohydroxyethyl dimethylhydantoin ester of coconut fatty acid (cocoate), or 3-hdyroxymethyl-5,5-dimethylhydantoin-1-yl-ethyl ester of coconut fatty acid [i.e., 3-hydroxymethyl-5,5-dimethyl-1,3-diazacyclopentane-2,4-dione-1-yl-ethyl ester of coconut fatty acid], or methylolated MHEDMH cocoate (I), was prepared from the non-methylolated MHEDMH cocoate (Ia) of Example B, as follows:

The MHEDMH coconut fatty acid ester (925 g, 2.60 mols), sodium bicarbonate (1 g), and paraformaldehyde (95% prills, 80 g, 2.65 mols) were added to a 1-liter 4 neck, flask. The flask was fitted with a mechanical stirrer, temperature control, and nitrogen sparge tube. With the nitrogen sparge set on low, the batch was heated to and held constant at 110° C. for 5 hours. At the end of this time, the batch had become clear and was allowed to cool to room temperature. The product was filtered (using a Sil Flo filter aid).

Final analysis showed the material [ester (I)] to be a viscous liquid at room temperature, with a color (Lovibond) of 15 yellow/2.5 red, total available formaldehyde (TF) content of 8.4%, free formaldehyde (FF) content of 0.51%, and water content of 0.1%.

The yield of 3-hydroxymethyl-5,5-dimethyl-1,3-diazacyclopentane-2,4-dione-1-yl-ethyl ester of coconut fatty acid [ester (I)] was 984 g (98% of the theoretical yield of 1,005 g).

Infra Red (neat) showed: 3485 (br), 1785 (sharp), 1720 (br), 1160 (br), and 1030 (br).

The same procedure was used to prepare the esters (I) of the other fatty acids in Table 1, and of isostearic acid.

Table 3 shows some physical properties of these esters (I).

TABLE 3

Physical Properties of Methylolated MHEDMH Esters (I) of the Invention

| Acid Used To Prepare Ester | Appearance at 25° C. | Melting Point °C. | Viscosity (cts) at 25° C. | TF Wt. % | FF Wt. % |
|---|---|---|---|---|---|
| Acetic | Clear Liquid | — | 4,384 | 12.3 | 0.6 |
| $C_{8/10}$ | Clear Liquid | — | 525 | 8.9 | 0.1 |
| Lauric | White Solid | <30 | — | 8.0 | 0.2 |
| Coconut | Clear Liquid | — | 544 | 7.8 | 0.1 |
| Oleic | Clear Liquid | — | 501 | 6.5 | 0.2 |
| Isostearic | Clear Liquid | — | 957 | 6.2 | 0.2 |
| Stearic | White Solid | 41.5 | — | 6.4 | 0.2 |

TF = Total available formaldehyde
FF = Free formaldehyde.

The esters (I) are all liquids, except for the (+98% pure) lauric ester and stearic ester which are solids, and apart from the acetic ester have a viscosity <1000 centistokes.

The total available formaldehyde (TF) in each ester (I), consequent methylolation, was found to equal the amount of formaldehyde initially reacted. Thus, whether the formaldehyde content is chemically bonded to the hydantoin moiety or is free formaldehyde (FF) in solution, e.g., in water as formaldehyde or methylene glycol $[CH_2(OH)_2]$, it remains available for biocidal action. Due to this direct relation, the weight percent TF in a given preparation of the ester (I), e.g. a cosmetic formulation, can be predicted accurately, regardless of the level of dilution.

For example, the cocoate (I) and oleate (I), at a concentration of 0.8% and 1.0%, respectively, both have a 0.4 wt. % TF.

The level of FF, as formaldehyde or methylene glycol, for the esters (I) as noted in Table 3 is impressively low compared to known formaldehyde releasing biocides. On average, the FF levels for the esters (I) are less than 0.6% per Table 3. This is equivalent to roughly 7-10% of the TF being present as FF.

Table 4 shows the FF levels of typical esters (I) determined at 1% active concentration in water and their ratios to TF.

TABLE 4

Free Formaldehyde Levels At 1% Active Concentration of Methylolated MHEDMH Esters (I) of the Invention

| Acid Used To Prepare Ester | Calculated TF, Wt. % | Determined FF, Wt. % | Ratio FF/TF |
|---|---|---|---|
| Acetic | 0.123 | 0.0199 | 0.162 |
| $C_{8/10}$ | 0.089 | 0.0116 | 0.131 |
| Coconut | 0.078 | 0.0113 | 0.145 |
| Oleic | 0.065 | 0.0112 | 0.172 |
| Isostearic | 0.062 | 0.0082 | 0.132 |
| Stearic | 0.064 | 0.0066 | 0.103 |

Thus, in aqueous media at dilute concentrations, such as a 1% solution in water, the FF/TF ratio is about 0.15 per Table 4, such that about 15% of the total formaldehyde is available as FF.

Tests with the acetate (I) at various dilutions in water show that the FF/TF ratio remains relatively constant, amounting to about 0.15% at concentration levels >5%. However, on decreasing the concentration to 1% and 0.1%, respectively, this ratio correspondingly increases to 0.20 and 0.25. Tests with the other esters (I) yield similar FF/TF ratio levels at these same low 1% and 0.1% concentrations. Thus, de-methylolation of the ester (I) to ester (Ia) appears to be suppressed when the ester (I) is at higher concentrations than about 1% in the given formulation.

Table 5 shows the solubilities, in grams (g), of the esters (I) in typical solvents.

TABLE 5

Solubilities of Methylolated MHEDMH Esters (I) of the Invention

| Acid Used To Prepare Ester | Water | Solvent at 25° C. Isopropyl Alcohol | Mineral Oil |
|---|---|---|---|
| Acetic | S | S | 3 g |
| $C_{8/10}$ | D | S | S |
| Lauric | D | S | S |
| Coconut | D | S | S |
| Oleic | D | S | S |
| Isostearic | D | S | S |
| Stearic | <1 g | S | S |

D = Dispersion
I = <0.1 g/100 g Solvent
S = >10 g/100 g Solvent.

It is clear from Table 5 that the higher esters (I) are readily dispersed in water, and soluble in organic solvents, permitting their convenient use in typical cosmetic or other personal care formulations, household product formulations, and industrial liquids.

SURFACE TENSION

Surface tension tests were conducted as to the relationship between the fatty acid aliphatic chain length, i.e. number of carbon atoms, in the esters (I), and their performance as surfactants. The length of the hydrophobic chain of a molecule is considered the major contributing factor to the critical micelle concentration (cmc) value of a surfactant. This value is obtained from surface tension measurement data. The lower the cmc, the more readily the material will form micelles.

The Gibbs' Free Energy of Micellation ($\Delta G°_{cmc}$) and the $\Delta G°_{cmc}$ per —$CH_2$— can be determined if the cmc is known.

The $\Delta G°_{cmc}$ is a calculated value obtained by Equation 1.

$$\Delta G°_{cmc} = 2.303RT(\log cmc - \log[water]) \quad \text{(Eq. 1)}$$

where
T = 298° K.;
R = 8.31 kJ/mol/°K.;
[water] = 55 mol/L;
and $\Delta G°_{cmc}$ units = kJ/mol.

The $\Delta G°_{cmc}$ per —$CH_2$— value is obtained from the slope of the straight line curve formed from a plot of $\Delta G°_{cmc}$ versus the number of carbon atoms in the lipophilic chain.

The $\Delta G°_{cmc}$, $\Delta G°_{cmc}$ per —$CH_2$— and cmc all reflect the energetics for micelle formation. The more negative these numbers, the greater the energetics for micelle formation.

Table 6 shows pertinent surface active properties in relation to the average number of carbon atoms in the lipophilic aliphatic (alkyl or alkenyl) chain of the fatty acid moiety, of typical esters (I) compared to typical known surfactants.

TABLE 6
Physical and Surface Active Properties of Methylolated MHEDMH Esters (I) of the Invention

| Acid Used To Prepare Ester | cmc (mol dm$^{-3}$) | $\Delta G°_{cmc}$ (kJ mol$^{-1}$) | n-Alkyl or n-Alkenyl Chain Length |
|---|---|---|---|
| Acetic | 7.24 × 10$^{-3}$ | −16.30 | 1.0 |
| C$_{8/10}$ | 1.2 × 10$^{-3}$ | −24.43 | 8.02 |
| Coconut | 1.0 × 10$^{-4}$ | −32.54 | 11.7 |
| Oleic | 4.0 × 10$^{-4}$ | −29.13 | 16.28 |
| Isostearic | 3.0 × 10$^{-4}$ | −29.83 | 17 |
| Stearic | 7.0 × 10$^{-3}$ | −22.08 | 16.98 |
| SLS | 4.4 × 10$^{-3}$ | −23.23 | — |
| POE 30 ML | 8.7 × 10$^{-4}$ | −33.30 | — |

SLS = Sodium lauryl sulfate
POE 30 ML = Polyoxyethylene 30 monolaurate (Polyoxyl-30-laurate).

Table 6 shows that of the esters (I) examined, the coconut, oleic and isostearic esters gave the lowest cmc values, with the coconut ester (cocoate) being lowest of all. The average aliphatic chain length for the coconut fatty acid is 11.7 carbon atoms, reflecting that maximization of the relevant properties occurs at about this number of carbon atoms. As with the cmc values, the oleic, isostearic and coconut esters (I) gave the lowest $\Delta G°_{cmc}$ values. As noted earlier, the more negative the $\Delta G°_{cmc}$, the greater the energetics for micelle formation.

Each of these esters had a significant $\Delta G°_{cmc}$ compared to the known surfactants shown in Table 6, sodium lauryl sulfate (SLS) and POE 30 monolaurate (POE 30 ML) having a $\Delta G°_{cmc}$ equal to −23.23 and −33.30 kJ/mol, respectively. However, the $\Delta G°_{cmc}$ [—CH$_2$—] value is greater by about 0.5 kJ/mol/[—CH$_2$—] than is usually observed for surfactants such as the sodium alkyl sulfates (2.39 kJ/mol) and the ethoxylated alcohols (2.5 kJ/mol).

This is clear from the drawing FIGURE of the curve obtained from a plot of the $\Delta G°_{cmc}$ values versus the number of carbon atoms in the lipophilic chain that gives the $\Delta G°_{cmc}$ [—CH$_2$—] value. The first part of the plot from C$_2$ to coco is linear (straight line) and yields a −1.5 kJ/mol for each CH$_2$ group in the lipophilic portion of the molecule. At a chain length of 12 (coco ester), the slope of the curve markedly decreases, but from the coconut to isostearic ester, there is little difference between the compounds as to their ability to form micelles.

The more positive value for the stearic ester, compared to the oleic and isostearic esters, per the drawing FIGURE as to micelle formation, may be explained by the fact that the stearic ester is far less soluble in water than the other such esters, which results in a lower Gibb's Free Energy of Micellation.

The cmc values were based on surface tension tests conducted with a tensiometer (Cenco-DuNoug Precision Model #70535, direct reading model) to determine the upward surface tension at the liquid-air surface of the test ester/water solution. The methods used to calibrate the tensiometer, calculate the "correction factor" (used to correct for the difference between the apparent and true surface tension), and collect data, were conducted as described in the manual for the instrument. Sodium lauryl sulfate (SLS) and distilled water were used as reference samples.

On completing data collection, plots of the surface tension (dynes) versus −log of the concentration (mols/liter) were prepared, using only the "corrected" surface tension value, obtained by applying the noted "correction factor" in each case. The "correction factor" value was found by multiplying the "apparent" surface tension by a calculated correction factor.

The critical micelle concentration (cmc) for each sample was determined by locating the point in the curve where the surface tension first begins to level off, per a known procedure.

HLB

Hydrophilic-Lipophilic Balance or HLB is a means of associating the hydrophilic and lipophilic characteristics between two surfactants. A "weighted average" method was used to determine the HLB of the esters (I), and by comparison of the precursor ester (Ia), in which two emulsifiers of known HLB values along with the test ester were incorporated in a mixture of mineral oil and water. Evaluation and HLB determination of each of a series of prepared emulsion samples were effected by visual inspection.

The HLB of the mixture "m" is calculated from the sum of the HLB contributions of each surfactant, "a", "b", "c", per Equation 2 which describes a system of oil, water, and three surfactants.

$$[HLB]m = [HLB]a(3-X)/4 + [HLB]b(X)/4 + [HLB]c(1)/4 \quad \text{(Eq. 2)}$$

where [HLB]m, [HLB]a, [HLB]b, and [HLB]c are the HLB values for the mixture "m", surfactant "a", surfactant "b", and surfactant "c", respectively, and X is the weight percent of "b" in "m".

Given that [HLB]m, [HLB]a, and [HLB]b, are known, and the ideal amount of "a", "b", and "c" to prepare a perfect emulsion has been determined, then by rearrangement of Eq. 2, the HLB of "c" can be calculated by Equation 3.

$$[HLB]c = 4[HLB]m - [HLB]a(3-x) - [HLB]b(X) \quad \text{(Eq. 3)}$$

To obtain the HLB of the test ester as surfactant "c", a series of formulations was prepared in which the known surfactant sorbitan monostearate (SMS) as "a" and the known surfactant POE 20 sorbitan monostearate (POE 20 SMS) as "b" were varied in amount (wt. %) relative to each other at a constant amount (1 wt. %) of "c", until an optimum emulsion was obtained. Different combinations of "a" and "b" were used to vary the HLB of "c", for emulsifying a 40:56 (wt. %) mixture of paraffin oil and distilled water (totaling 96 wt. %). Table 7 shows the sample amounts (wt. %) per Eq. 3 and known HLB values for "a", "b" and "m".

TABLE 7
General Formula For HLB Determination

| Ingredient | Wt. % in Sample | HLB |
|---|---|---|
| Sorbitan Monostearate, "a" | 3-X | 4.7 |
| POE 20 Sorbitan Monostearate, "b" | X | 14.9 |
| Test Ester, "c" | 1 | varied |
| Paraffin oil (Baker Grade, 350 SUS) | 40 | * |
| Distilled water | 56 | * |

*[HLB]m of 10.1 has been assigned to a perfectly emulsified 40:56 (wt. %) mixture of paraffin and water.

To prepare the emulsions, surfactants "a", "b", and "c", and the paraffin oil were combined in a 150 ml beaker and heated slowly with agitation to 70°-80° C. The value of "X" in each formulation was predetermined by rearranging Eq. 3 to solve for X, and then inserting into the equation various [HLB]c values for the test ester (i.e., 2, 3, 4, 5, 6 . . . ). The [HLB]c values chosen reflected a range that would likely contain the actual HLB of the test ester. Hot distilled water (70°-80° C.) was then slowly added with agitation. The total weight of all these reagents was 100 grams. The resulting emulsion was allowed to cool, with continued agitation, until the temperature dropped below 30° C.

A series of emulsions for each test was prepared, one at a time, and then examined as a set. Each sample within the series was evaluated and graded according to the quality of the emulsion by visual examination of droplet size. Table 8 shows the qualitative ranking used to grade the emulsions.

TABLE 8

| Emulsion Ranking For HLB Determination | |
|---|---|
| Ranking | Emulsion Quality |
| Excellent | White emulsion with strong illumination on the wall of the beaker |
| Good | White emulsion with illumination on the wall of the beaker |
| Poor | White emulsion with no illumination on the wall of the beaker |
| Bad | Phase separation or W/O-type emulsion. |

For example, a series of formulations was prepared to determine the HLB or HLB range for the oleate (Ia). Seven different samples were prepared, and X was calculated for a series of emulsions that varies in HLB number from 5 to 11. All samples were ranked from excellent to bad per Table 8. The best emulsion was from the formulation in which the test ester was assigned an HLB of 9, and the second best was from that in which the test ester was assigned an HLB of 8. The remaining five emulsions were ranked either poor or bad. As a result, the HLB range for the oleic ester (Ia) was assigned an HLB range of 8-9.

Table 9 shows the experimentally determined HLB values of the oleic ester (Ia) and typical other esters (Ia) and (I).

TABLE 9

| Experimentally Determined HLB of Non-Methylolated Esters (Ia) and Methylolated Esters (I) of the Invention | | |
|---|---|---|
| Acid Used To Prepare Ester | Average HLB | Range |
| Acetic | | |
| Non-Methylolated Ester | 7.0 | 6-8 |
| Methylolated Ester | 19.0 | 19-20 |
| $C_{8/10}$ | | |
| Non-Methylolated Ester | 7.0 | 6-8 |
| Methylolated Ester | 13.3 | 11-15 |
| Lauric | | |
| Non-Methylolated Ester | 6.5 | 5-7 |
| Methylolated Ester | 12.8 | 12-14 |
| Coconut | | |
| Non-Methylolated Ester | 6.0 | 5-7 |
| Methylolated Ester | 12.0 | 10-14 |
| Oleic | | |
| Non-Methylolated Ester | 8.5 | 8-9 |
| Methylolated Ester | 15.0 | 14-16 |
| Isostearic | | |
| Non-Methylolated Ester | 7.0 | 6-7 |
| Methylolated Ester | 15.0 | 14-16 |

TABLE 9-continued

| Experimentally Determined HLB of Non-Methylolated Esters (Ia) and Methylolated Esters (I) of the Invention | | |
|---|---|---|
| Acid Used To Prepare Ester | Average HLB | Range |
| Stearic | | |
| Non-Methylolated Ester | 1.5 | 1-3 |
| Methylolated Ester | 7.0 | 6-8 |

Table 9 shows that the non-methylolated esters (Ia) have HLB values that range from about 1 to 9, with a mean average range between about 6 to 8, the oleate (Ia) having the highest (average 8.5), and the stearate (Ia) having the lowest (average 1.5), HLB values. The esters (Ia), which are for the most part water insoluble, are effective O/W (oil-in-water) dispersing agents.

However, the methylolated esters (I) have HLB values that range from 6 to 20, with a mean average range between about 12 to 16, the acetate (I) having the highest (average 19), and the stearate (I) having the lowest (average 7), HLB values. The esters (I), which are for the most part water soluble or dispersible, are effective W/O (water-in-oil) dispersing agents.

EMULSION TESTS

Emulsion stability tests were performed on the esters (I), and for comparison on the precursor esters (Ia), to determine the extent to which each stabilized a standardized solution of water and an oil, using a common procedure consisting of homogenizing a mixture containing the test ester (2%), myristyl propionate (7%), and water (91%). While two emulsifiers are normally used to prepare a cosmetic formulation, e.g. one with a high HLB and the other with a low HLB, the test method herein using only one emulsifier, i.e. the test ester, is fully indicative of the emulsifying attributes of these esters.

The tests were performed with emulsions (500 g), prepared by combining the test ester (10.0 g), myristyl propionate (35 g), and distilled water (455 g) in a container and homogenizing the contents for one minute, via a Kika-Werk Ultra-Turrax S D-45 homogenizer. The emulsions were poured into a one pound flint jar, capped, and periodically examined over a 55 day period.

Table 10 shows the stabilizing properties of typical esters (I) and (Ia) determined by these emulsification tests.

TABLE 10

| Emulsification Tests of Non-Methylolated Esters (Ia) and Methylolated Esters (I) of the Invention | | | | |
|---|---|---|---|---|
| Acid Used To Prepare Ester | Classification of Emulsion Time After Preparation of Emulsion | | | |
| | 2 Hours | 7 Days | 22 Days | 55 Days |
| Acetic | | | | |
| Non-Meth. | 2-Phase | 2-Phase | 2-Phase | 2-Phase |
| Meth. | 2-Phase | 2-Phase | 2-Phase | 2-Phase |
| $C_{8/10}$ | | | | |
| Non-Meth. | OK | 2-Phase | 2-Phase | 2-Phase |
| Meth. | OK | Some Sep. | Some Sep. | 2-Phase |
| Coconut | | | | |
| Non-Meth. | OK | 2-Phase | 2-Phase | 2-Phase |
| Meth. | Best | Best | Best | Some Sep. |
| Oleic | | | | |
| Non-Meth. | OK | 2-Phase | 2-Phase | 2-Phase |
| Meth. | Good | Good | Good | Good |
| Isostearic | | | | |

TABLE 10-continued

Emulsification Tests of Non-Methylolated Esters (Ia) and Methylolated Esters (I) of the Invention

| Acid Used To Prepare Ester | Classification of Emulsion Time After Preparation of Emulsion | | | |
|---|---|---|---|---|
| | 2 Hours | 7 Days | 22 Days | 55 Days |
| Non-Meth. Stearic | OK | 2-Phase | 2-Phase | 2-Phase |
| Meth. Stearic | Good | Good | Good | Good |
| Non-Meth. | 2-Phase | 2-Phase | 2-Phase | 2-Phase |
| Meth. | Good/OK | OK | OK | OK |
| Blend of 93% Water and 7% Myristyl Propionate | Complete separation in less than 2 minutes. | | | |

Non-Meth. = Non-Methylolated MHEDMH Ester (Ia)
Meth. = Methylolated MHEDMH Ester (I)
OK (Fair) = Emulsion formed but some oil droplets present.
Good = Good emulsion, tends toward slight separation but will readily re-mix by rotating container (jar) vertically.
Best = Forms stable emulsion.

These emulsion tests show that the esters (Ia) are not effective to produce stable emulsions for more than 24 hours.

However, the esters (I) are effective, and can be accurately ranked from best to poorest emulsifier. The quality of the emulsion is determined by the overall stability and appearance of the emulsion, and the quality in decreasing order of rank was found as follows: cocoate, laurate > oleate, isostearate > stearate > $C_{8/10}$ ester- > acetate (total separation). The coconut and lauric acid esters were the best emulsifiers tested. They were able to stabilize emulsions for more than 22 days, whereas the $C_{8/10}$ ester and the acetate were generally unable to stabilize an emulsion for more than two hours.

The optimum emulsifying properties of the coconut, lauric, oleic and isosteaaric esters (I) follow the same trend of optimum, i.e. lowest cmc and $\Delta G°_{cmc}$, values for the coconut, oleic and isostearic esters (I) per the surface tension tests.

DISPERSION TESTS

The dispersion stability tests were performed on the esters (I) to determine the extent each was able to disperse itself in an aqueous medium.

The dispersions were prepared by homogenizing a mixture of the test ester and water, after which repeated examination of the sample was effected for a period of 55 days. This test method is fully indicative of the dispersibility of these esters (I).

The dispersion tests were performed with the esters at 0.5% and 5.0% active levels in water, prepared by combining the test ester with distilled water, and homogenizing the mixture for one to three minutes, via a Kika-Werk Ultra-Turrax S D-45 homogenizer. The dispersions were poured into an eight ounce flint jar, capped, and periodically examined over a 55 day period.

Table 11 shows the dispersion properties in water and oil phase mixtures of typical esters (I) at 0.5% and 5% active levels as determined by these dispersion tests.

TABLE 11

Dispersion Tests of Methylolated Esters (I) of the Invention

| Acid Used To Prepare Ester | Classification of Dispersion (0.5% and 5% Active) Time After Preparation of Dispersion | | | |
|---|---|---|---|---|
| | 2 Hours | 3 Days | 13 Days | 55 Days |
| Acetic 0.5% | Dissolved | Dissolved | Dissolved | Dissolved |
| 5.0% | Dissolved | Dissolved | Dissolved | Dissolved |
| $C_{8/10}$ | | | | |
| 0.5% | OK | OK | 2-Phase | 2-Phase |
| 5.0% | OK | OK | 2-Phase | 2-Phase |
| Coconut | | | | |
| 0.5% | Good | Good | OK | OK |
| 5.0% | Good | OK | OK | OK |
| Oleic | | | | |
| 0.5% | Best | Best | Best | Best |
| 5.0% | Best | Good | Good | Good |
| Isostearic | | | | |
| 0.5% | Best | Best | Best | Best |
| 5.0% | Best | Best | Best | Best |
| Stearic | | | | |
| 0.5% | OK | 2-Phase | 2-Phase | 2-Phase |
| 5.0% | OK | 2-Phase | 2-Phase | 2-Phase |

OK (Fair) = Dispersion formed but some oil droplets present.
Good = Good dispersion, tends toward slight separation but will readily re-mix by rotating container (jar) vertically.
Best = Forms stable dispersion.

It is clear from Table 11 that many of the esters (I) when homogenized in water produce dispersions that are stable for extended periods. Indeed, at 0.5%, and even 5%. active levels, the cocoate, laurate, oleate and isosterate esters (I) homogenized in water form dispersions that are stable for weeks, while those of the isostearate ester (I) are stable for months.

Using this dispersion test method, the esters (I) were accurately ranked from the best to the poorest. Their quality in decreasing order of rank was found as follows: isostearate > oleate > cocoate > laurate > $C_{8/10}$ ester > > stearate > acetate (total dissolution).

The optimum aqueous dispersion stability properties of the coconut, lauric, oleic and isostearic esters (I) follow the same trend of optimum, i.e. lowest cmc and $\Delta G°_{cmc}$, values, per the surface tension tests, and optimum emulsifying properties per the emulsifying tests, for the coconut, lauric, oleic and isostearic esters (I), as the case may be.

ANTIMICROBIAL TESTS

The antimicrobial properties of typical esters (I) and (Ia) were tested by minimum inhibitory concentration (MIC) tests, along with certain known substances, against three strains of organisms: a mold, *Aspergillus niger*; a gram-positive bacteria, *Staphylococcus aureus*; and two gram-negative bacteria, *Escherichia coli* and *Pseudomonas aeruginosa*. All the microorganisms chosen are suggested by the CTFA (Cosmetic Toiletry Fragrance Association) for use in initial screening tests. These tests were used to determine any effect on biocidal activity of the varying chain length of the ester.

The known substances, on which identical tests were also performed, included the biocide, dimethyloldimethylhydantoin or DMDMH (iv), and a series of three surfactants, i.e., the three common emulsifiers, sodium lauryl sulfate (SLS); ethylene glycol distearate (EGDS), in the form of the commercial product PEGOSPERSE 50 DS (Lonza Inc.); and polyoxyethylene 20 sorbitan monoleate (POE 20 SMO), in the form of the commercial product GLYCOSPERSE 0 20 (Lonza Inc.).

The tests entailed contaminating a preexisting microcolony with a known quantity (ppm, concentration) of test material. Each colony was then examined periodically over a one week period. An efficacious test resulted in the kill of the entire colony. A test was deemed non-efficacious when there was no decrease in colony size. In an effort to avoid any possible solvent effect, the micro-study was conducted in a totally aqueous solvent system without use of any other solvent.

Table 12 shows the results of the antimicrobial study against the mold, *Aspergillus niger*.

TABLE 12

Antimicrobial Study of Non-Methylolated Esters (Ia) and Methylolated Esters (I) of the Invention Against *Aspergillus niger* (Mold)

| Test Material | Concentration ppm | TF ppm | Day (Colony Count* × 1,000) | | | | |
|---|---|---|---|---|---|---|---|
| | | | 0 | 1 | 2 | 3 | 7 |
| Methylolated $C_{8/10}$ Ester | 10,800 | 955 | 200 | 20 | 20 | 4 | 2 |
| Methylolated Lauric Ester | 11,400 | 890 | 400 | 2 | <0.01 | <0.01 | <0.01 |
| Non-Methylolated Lauric Ester | 14,700 | — | 300 | 200 | 200 | 220 | 150 |
| Methylolated Oleic Ester | 14,700 | 955 | 2,000 | 0.5 | <0.01 | <0.01 | <0.01 |
| DMDMH (iv)* | 3,000 | 956 | 400 | <0.03 | <0.01 | <0.01 | <0.01 |
| SLS | 14,700 | — | 600 | 2,000 | 300 | 160 | 200 |
| EGDS | 14,700 | — | 2,000 | 500 | 300 | 200 | 700 |
| POE 20 SMO | 14,700 | — | 700 | 400 | 120 | 210 | 300 |
| Blank (water) | — | — | 2,000 | 300 | 2,000 | 3,000 | 600 |

SLS = Sodium lauryl sulfate
EGDS = Ethylene glycol distearate
POE 20 SMO = Polyoxyethylene 20 sorbitan monooleate
*Colony count before adding test material was too numerous to count (TNC).

Table 13 shows the results of the antimicrobial study against the gram-positive bacteria, *Staphylococcus aureus*.

TABLE 13

Antimicrobial Study of Non-Methylolated Esters (Ia) and Methylolated Esters (I) of the Invention Against *Staphylococcus aureus* (Gram-Positive Bacteria)

| Test Material | Concentration ppm | TF ppm | Day (Colony Count* × 1,000) | | | | |
|---|---|---|---|---|---|---|---|
| | | | 0 | 1 | 2 | 3 | 7 |
| Methylolated $C_{8/10}$ Ester | 10,800 | 955 | TNC | TNC | <0.01 | <0.01 | <0.01 |
| Methylolated Lauric Ester | 11,400 | 890 | TNC | 4,000 | <0.01 | <0.01 | <0.01 |
| Non-Methylolated Lauric Ester | 14,700 | — | TNC | 500 | 3,000 | TNC | 30 |
| Methylolated Oleic Ester | 14,700 | 955 | TNC | 4,200 | <0.01 | <0.01 | <0.01 |
| DMDMH (iv)* | 3,000 | 956 | TNC | TNC | TNC | <0.01 | <0.01 |
| SLS | 14,700 | — | 2,000 | 3,000 | TNC | 450 | <0.01 |
| EGDS | 14,700 | — | 600 | 350 | TNC | TNC | 2,000 |
| POE 20 SMO | 14,700 | — | 4,000 | 4,500 | 3,200 | 26,000 | 3,000 |
| Blank (water) | — | — | TNC | TNC | 5,000 | 13,000 | 12,000 |

SLS = Sodium lauryl sulfate
EGDS = Ethylene glycol distearate
POE 20 SMO = Polyoxyethylene 20 sorbitan monooleate
TNC = Too Numerous To Count
*Colony count before adding test material was TNC × 1,000.

Table 14 shows the results of the antimicrobial study against the gram-negative bacteria, *Escherichia coli*.

TABLE 14

Antimicrobial Study of Non-Methylolated Esters (Ia) and Methylolated Esters (I) of the Invention Against *Escherichia coli* (Gram-Negative Bacteria)

| Test Material | Concentration ppm | TF ppm | Day (Colony Count* × 1,000) | | | | |
|---|---|---|---|---|---|---|---|
| | | | 0 | 1 | 2 | 3 | 7 |
| Methylolated $C_{8/10}$ Ester | 10,800 | 955 | TNC | TNC | <0.01 | <0.01 | <0.01 |
| Methylolated Lauric Ester | 11,400 | 890 | TNC | TNC | <0.01 | <0.01 | <0.01 |
| Non-Methylolated Lauric Ester | 14,700 | — | TNC | TNC | TNC | TNC | TNC |
| Methylolated Oleic Ester | 14,700 | 955 | 4,000 | <0.01 | <0.01 | <0.01 | <0.01 |
| DMDMH (iv)* | 3,000 | 956 | TNC | TNC | TNC | <0.01 | <0.01 |
| SLS | 14,700 . | — | 8,000 | 20 | TNC | 160 | 60 |
| EGDS | 14,700 | — | 2,000 | TNC | TNC | TNC | TNC |

TABLE 14-continued

Antimicrobial Study of Non-Methylolated Esters (Ia)
and Methylolated Esters (I) of the Invention Against
*Escherichia coli* (Gram-Negative Bacteria)

| Test Material | Concentration ppm | TF ppm | Day (Colony Count* × 1,000) | | | | |
|---|---|---|---|---|---|---|---|
| | | | 0 | 1 | 2 | 3 | 7 |
| POE 20 SMO | 14,700 | — | 2,000 | TNC | TNC | TNC | TNC |
| Blank (water) | — | — | TNC | TNC | 4,600 | TNC | TNC |

SLS = Sodium lauryl sulfate
EGDS = Ethylene glycol distearate
POE 20 SMO = Polyoxyethylene 20 sorbitan monooleate
TNC = Too Numerous To Count
*Colony count before adding test material was TNC × 1,000.

Table 15 shows the results of the antimicrobial study against the gram-negative bacteria, *Pseudomonas aeruginosa*.

TABLE 15

Antimicrobial Study of Non-Methylolated Esters (Ia)
and Methylolated Esters (I) of the Invention Against
*Pseudomonas aeruginosa* (Gram-Negative Bacteria)

| Test Material | Concentration ppm | TF ppm | Day (Colony Count* × 1,000) | | | | |
|---|---|---|---|---|---|---|---|
| | | | 0 | 1 | 2 | 3 | 7 |
| Methylolated $C_{8/10}$ Ester | 10,800 | 955 | TNC | TNC | <0.01 | <0.01 | <0.01 |
| Methylolated Lauric Ester | 11,400 | 890 | TNC | <0.01 | <0.01 | <0.01 | <0.01 |
| Non-Methylolated Lauric Ester | 14,700 | — | TNC | TNC | TNC | 250 | TNC |
| Methylolated Oleic Ester | 14,700 | 955 | TNC | <0.01 | <0.01 | <0.01 | <0.01 |
| DMDMH (iv)* | 3,000 | 956 | TNC | TNC | <0.01 | <0.01 | <0.01 |
| SLS | 14,700 | — | 4,100 | 500 | TNC | 30 | 50 |
| EGDS | 14,700 | — | 3,000 | TNC | TNC | 2,500 | TNC |
| POE 20 SMO | 14,700 | — | 2,000 | TNC | TNC | 2,200 | TNC |
| Blank (water) | — | — | TNC | TNC | TNC | TNC | TNC |

SLS = Sodium lauryl sulfate
EGDS = Ethylene glycol distearate
POE 20 SMO = Polyoxyethylene 20 sorbitan monooleate
TNC = Too Numerous To Count
*Colony count before adding test material was TNC × 1,000.

At the same TF level recommended for the formaldehyde donor DMDMH (iv), the esters (I), which are monomethylolated, were surprisingly found to be as effective as DMDMH (iv), which is dimethylolated.

All the esters (I) tested were found biocidally effective against the mold, and gram-positive and gram-negative bacteria.

The presence of the long aliphatic fatty acid chain in the molecule of the esters (I) is unexpectedly shown not to detract from or interfere with their biocidal action. Their formaldehyde content appears to release or act in like biocidal manner to that in DMDMH (iv), and in some instances they perform more effectively than the latter, despite the presence of such long aliphatic chain, yet the free formaldehyde levels for the esters (I) is impressively low compared to known formaldehyde releasing biocides in general. At the same time, the esters (I) provide significant surfactant properties, especially due to their broad HLB range and effective emulsification behavior.

The results shows that none of the three known long aliphatic chain containing emulsifiers, sodium lauryl sulfate, ethylene glycol distearate and POE 20 sorbitan monooleate, was effective as a biocide against the organism under the test conditions.

Although only the results of the non-methylolated laurate (Ia) are given in Tables 12–15, all the esters (Ia) were found not to be effective against these organisms under the test conditions, indicating that the active biocidal effect of the esters (I) is traceable to release of formaldehyde donated by their methylolated moiety, which is absent from the esters (Ia).

Microbiological challenge tests were also conducted with the lauric and oleic esters (I), representing molecules having $C_{12}$ and $C_{18}$ aliphatic fatty acid chain length moieties, respectively.

These preservative challenge tests were used to determine the biocidal performance of these two esters (I) in aqueous solution and dispersion formulations inoculated with a given one of two test organisms, previously isolated from a contaminated calcium carbonate ($CaCO_3$) dispersion, i.e. gram-positive bacteria, designated Staphylococcus species a and Staphylococcus species b, as compared to three known biocides or preservatives, designated as DANTOGARD (trademark), Tektamer 38 (1,2-dibromo-2,4-dicyanobutane) and Nuodex PMA-18.

The solution formulation was represented by the inclusion of the test sample as preservative system in deionized water, and the dispersion formulation was represented by the inclusion of the test sample as preservative system in a $CaCO_3$ aqueous dispersion (identified as Hydrocarb 60), the latter typifying a dispersed pigment medium, e.g. as used in a paint or other industrial dispersion or slurry. The antimicrobial activity of the test samples was evaluated at individually selective concentrations.

Table 16 shows the preservative systems added to the deionized water (System A) and to the $CaCO_3$ aqueous dispersions (System B), and their individual percentage concentrations, as used in these preservative challenge tests.

TABLE 16

| Sample No. | | Preservative Systems | |
|---|---|---|---|
| System A | System B | Preservative | % Active |
| 1A | 1B | DANTOGARD | 0.2 |
| 2A | 2B | DANTOGARD | 0.4 |
| 3A | 3B | Tektamer 38 | 0.01 |
| 4A | 4B | Tektamer 38 | 0.025 |
| 5A | 5B | Nuodex PMA-18 | 0.05 |
| 6A | 6B | Methylolated Oleic Ester | 1.25 |
| 7A | 7B | Methylolated Oleic Ester | 3.0 |
| 8A | 8B | Methylolated Lauric Ester | 1.25 |
| 9A | 9B | Methylolated Lauric Ester | 3.0 |
| 10A | 10B | Water Control | — |

Of these 20 aqueous liquid samples, deionized water samples 1A to 5A were all clear liquids (indicating total solubility), and deionized water samples 6A to 9A were all white cloudy liquids (indicating less than total solubility), sample 10A serving as blank or control, while calcium carbonate aqueous samples 1B to 10B were all white liquids (pigment dispersions).

All these liquid samples were stored at room temperature until the start of the tests. The test organisms were maintained or nutrient agar at 4° C. and subcultured in nutrient broth (Difco), and a 24 hour culture incubated at 35° C. was used for the testing over a challenge test time period of 14 days.

The test formulations were prepared per a standardized procedure, by placing 20 ml aliquots of the stored sample into sterile test tubes, and then adding 0.1 ml of a standardized $10^6$ suspension of a 24 hour culture in nutrient broth. Plate counts were taken immediately to determine the initial level of the microbial population, and the containers were incubated at 20°–25° C. Plate counts were retaken at 1, 3, 7 and 14 days, with the final reductions being calculated from the 14 days results.

Table 17 shows the results of the preservative challenge test against gram-positive bacteria, Staphylococcus species a, in deionidized water.

TABLE 17

Preservative Challenge Test of Methylolated Esters (I) of the Invention Against Staphylococcus species a in Deionized Water
Initial Plate Count: $9.6 \times 10^6$ Colony Forming Units per ml
Total Plate Count:

| | Colony Forming Units per ml | | | | | % Reduction |
|---|---|---|---|---|---|---|
| Sample | Day 0* | Day 1 | Day 3 | Day 7 | Day 14 | |
| 1A | $7.9 \times 10^4$ | <10 N.D.** | <10 N.D. | <10 N.D. | <10 N.D. | 100 |
| 2A | $9.6 \times 10^4$ | <10 N.D. | <10 N.D. | <10 N.D. | <10 N.D. | 100 |
| 3A | $8.2 \times 10^3$ | $8.5 \times 10^2$ | <10 N.D. | <10 N.D. | <10 N.D. | 100 |
| 4A | $1 \times 10^4$ | <10 N.D. | <10 N.D. | <10 N.D. | <10 N.D. | 100 |
| 5A | $1 \times 10^3$ | <10 N.D. | <10 N.D. | <10 N.D. | <10 N.D. | 100 |
| 6A | $1.7 \times 10^4$ | <10 N.D. | <10 N.D. | <10 N.D. | <10 N.D. | 100 |
| 7A | $1.3 \times 10^4$ | <10 N.D. | <10 N.D. | <10 N.D. | <10 N.D. | 100 |
| 8A | $7.3 \times 10^4$ | <10 N.D. | <10 N.D. | <10 N.D. | <10 N.D. | 100 |
| 9A | $1.8 \times 10^4$ | <10 N.D. | <10 N.D. | <10 N.D. | <10 N.D. | 100 |
| 10A | $9.6 \times 10^3$ | $1.9 \times 10^4$ | $3.1 \times 10^4$ | $1.7 \times 10^4$ | $6.2 \times 10^3$ | — |

*Day 0 counts were performed 30-60 seconds after inoculation.
**N.D. = None Detected
Note: The percent reduction was calculated from the initial plate counts and the 14 day results.

Table 18 shows the results of the preservative challenge test against gram-positive bacteria, Staphylococcus species b, in deionized water.

TABLE 18

Preservative Challenge Test of Methylolated Esters (I) of the Invention Against Staphylococcus species b in Deionized Water
Initial Plate Count: $2.0 \times 10^6$ Colony Forming Units per ml
Total Plate Count:

| | Colony Forming Units per ml | | | | | % Reduction |
|---|---|---|---|---|---|---|
| Sample | Day 0* | Day 1 | Day 3 | Day 7 | Day 14 | |
| 1A | $1.8 \times 10^4$ | <10 N.D.** | <10 N.D. | <10 N.D. | <10 N.D. | 100 |
| 2A | $1.7 \times 10^4$ | <10 N.D. | <10 N.D. | <10 N.D. | <10 N.D. | 100 |
| 3A | $5.5 \times 10^3$ | $1.1 \times 10^3$ | <10 N.D. | <10 N.D. | <10 N.D. | 100 |
| 4A | $6 \times 10^3$ | <10 N.D. | <10 N.D. | <10 N.D. | <10 N.D. | 100 |
| 5A | $2 \times 10^3$ | <10 N.D. | <10 N.D. | <10 N.D. | <10 N.D. | 100 |
| 6A | $1.4 \times 10^4$ | <10 N.D. | <10 N.D. | <10 N.D. | <10 N.D. | 100 |
| 7A | $7.3 \times 10^3$ | <10 N.D. | <10 N.D. | <10 N.D. | <10 N.D. | 100 |
| 8A | $1.5 \times 10^4$ | <10 N.D. | <10 N.D. | <10 N.D. | <10 N.D. | 100 |
| 9A | $1.8 \times 10^4$ | <10 N.D. | <10 N.D. | <10 N.D. | <10 N.D. | 100 |
| 10A | $1.2 \times 10^4$ | $1.2 \times 10^5$ | $3.2 \times 10^6$ | $2.1 \times 10^6$ | $2.7 \times 10^6$ | — |

*Day 0 counts were performed 30-60 seconds after inoculation.
**N.D. = None Detected
Note: The percent reduction was calculated from the initial plate counts and the 14 day results.

Table 19 shows the results of the preservative challenge test against gram-positive bacteria, Staphylococcus species a, in $CaCO_3$ aqueous dispersions.

TABLE 19

Preservative Challenge Test of Methylolated Esters (I) of the
Invention Against Staphylococcus species a in $CaCO_3$ Aqueous Dispersions
Initial Plate Count: $3.6 \times 10^6$ Colony Forming Units per ml
Total Plate Count:

| Sample | Colony Forming Units per ml | | | | | % Reduction |
|---|---|---|---|---|---|---|
| | Day 0* | Day 1 | Day 3 | Day 7 | Day 14 | |
| 1B | $1.4 \times 10^5$ | <10 N.D.** | <10 N.D. | <10 N.D. | <10 N.D. | 100 |
| 2B | $1.9 \times 10^5$ | <10 N.D. | <10 N.D. | <10 N.D. | <10 N.D. | 100 |
| 3B | $1.1 \times 10^5$ | $8.5 \times 10^2$ | <10 N.D. | <10 N.D. | <10 N.D. | 100 |
| 4B | $1.6 \times 10^5$ | <10 N.D. | <10 N.D. | <10 N.D. | <10 N.D. | 100 |
| 5B | <10 N.D. | <10 N.D. | <10 N.D. | <10 N.D. | <10 N.D. | 100 |
| 6B | $5.2 \times 10^4$ | <10 N.D. | <10 N.D. | <10 N.D. | <10 N.D. | 100 |
| 7B | $2.9 \times 10^6$ | <10 N.D. | <10 N.D. | <10 N.D. | <10 N.D. | 100 |
| 8B | $1.1 \times 10^6$ | $9.5 \times 10^3$ | <10 N.D. | $6 \times 10^2$ | $2.1 \times 10^3$ | — |
| 9B | $5.6 \times 10^4$ | $5.0 \times 10^3$ | <10 N.D. | $9 \times 10^3$ | $1.3 \times 10^4$ | — |
| 10B | $2.3 \times 10^6$ | $3.2 \times 10^4$ | $3.6 \times 10^4$ | $6.0 \times 10^2$ | $6.0 \times 10^2$ | — |

*Day 0 counts were performed 30–60 seconds after inoculation.
**N.D. = None Detected
Note: The percent reduction was calculated from the initial plate counts and the 14 day results.

Table 20 shows the results of the preservative challenge test against gram-positive bacteria, Staphylococcus species b, in $CaCO_3$ aqueous dispersions.

TABLE 20

Preservative Challenge Test of Methylolated Esters (I) of the
Invention Against Staphylococcus species b in $CaCO_3$ Aqueous Dispersions
Initial Plate Count: $23 \times 10^6$ Colony Forming Units per ml
Total Plate Count:

| Sample | Colony Forming Units per ml | | | | | % Reduction |
|---|---|---|---|---|---|---|
| | Day 0* | Day 1 | Day 3 | Day 7 | Day 14 | |
| 1B | $2.7 \times 10^6$ | <10 N.D.** | <10 N.D. | <10 N.D. | <10 N.D. | 100 |
| 2B | $1.1 \times 10^6$ | <10 N.D. | <10 N.D. | <10 N.D. | <10 N.D. | 100 |
| 3B | $2.8 \times 10^6$ | $1.1 \times 10^3$ | <10 N.D. | <10 N.D. | <10 N.D. | 100 |
| 4B | $5.5 \times 10^5$ | <10 N.D. | <10 N.D. | <10 N.D. | <10 N.D. | 100 |
| 5B | <10 N.D. | <10 N.D. | <10 N.D. | <10 N.D. | <10 N.D. | 100 |
| 6B | $5.1 \times 10^5$ | $8.5 \times 10^2$ | <10 N.D. | <10 N.D. | <10 N.D. | 100 |
| 7B | $2.8 \times 10^6$ | <10 N.D. | <10 N.D. | <10 N.D. | <10 N.D. | 100 |
| 8B | $5.5 \times 10^5$ | $7.4 \times 10^3$ | <10 N.D. | $9 \times 10^3$ | $1.2 \times 10^4$ | — |
| 9B | $3.1 \times 10^4$ | $1.6 \times 10^4$ | <10 N.D. | $1.2 \times 10^4$ | $1.8 \times 10^4$ | — |
| 10B | $1.9 \times 10^6$ | $2.3 \times 10^7$ | $9.9 \times 10^6$ | $1.5 \times 10^7$ | $3.2 \times 10^7$ | — |

*Day 0 counts were performed 30–60 seconds after inoculation.
**N.D. = None Detected
Note: The percent reduction was calculated from the initial plate counts and the 14 day results.

Tables 17 and 18 show that the end of the 14 day period both the oleic and lauric esters (I) [Samples 6A-9A] are effective as preservatives in water against microorganisms as typified by the stated Staphylococcus species a and b at the active concentration levels tested.

On the other hand, Tables 19 and 20 show that at the end of the 14 day period while the oleic ester (I) [Samples 6B-7B] is effective as a preservative in calcium carbonate aqueous dispersions against such microorganisms at the active concentration levels tested, the lauric ester (I) [Samples 8B-9B] is not.

This is indicative of the fact that the longer aliphatic fatty acid chain moiety of the oleate (I) enhances both the biocidal and surfactant properties of the given hydantoin molecule, and that to achieve a comparable level of dual biocidal and surfactant effectiveness a higher concentration of the correspondingly decreased length aliphatic fatty acid chain moiety laurate (I) should be used in the product formulation.

COD AND BOD ANALYSIS

Chemical oxygen demand (COD) values for typical esters (Ia) and (I), and biochemical oxygen demand (BOD) values for such esters (I), are shown in Table 21.

TABLE 21

COD and BOD of Non-Methylolated Esters (Ia) and Methylolated Esters (I) of the Invention

| Acid Used To Prepare Ester | Calculated COD | Determined | |
|---|---|---|---|
| | | COD | BOD |
| Acetic | | | |
| Non-Methylolated Ester | 1.57 | 1.32 | — |
| Methylolated Ester | 1.51 | 0.41 | 0.026 |
| $C_{8/10}$ | | | |
| Non-Methylolated Ester | 2.33 | 1.60 | — |
| Methylolated Ester | 2.22 | 0.50 | 0.41 |
| Coconut | | | |
| Non-Methylolated Ester | 2.30 | 1.04 | — |
| Methylolated Ester | 2.20 | 0.49 | 0.34 |
| Oleic | | | |
| Non-Methylolated Ester | 2.54 | 1.37 | — |
| Methylolated Ester | 2.45 | 1.10 | 0.34 |
| Isostearic | | | |
| Non-Methylolated Ester | 2.44 | 0.81 | — |
| Methylolated Ester | 2.36 | 0.90 | 0.77 |
| Stearic | | | |
| Non-Methylolated Ester | 2.51 | 1.13 | — |
| Methylolated Ester | 2.42 | 1.22 | 0.27 |

These results show that the esters (I) appear to be suitably biodegradable.

Based on the foregoing, typical approximate proportional amount product formulations of the testers (I) contemplate the follows:

| | |
|---|---|
| 1. Low Solids High Foam Shampoo (Personal Care Product): | |
| 30.0% | Ammonium lauryl sulfate |
| 3.0% | Cocodimethylamine oxide |
| 0.4% | Citric acid |
| 2.0% | Ester (I) |
| Remainder | Water, deionized |
| 2. Fabric Softener (Household Product): | |
| 4.0% | Ditallow-diamidomethosulfate (Softener) |
| 1.5% | Ester (I) |
| Remainder | Water |
| 3. Pigment Dispersion (Industrial Product): | |
| 5.0% | Ester (I) |
| Remainder | Aqueous calcium carbonate pigment dispersion. |

What is claimed is:

1. Composition comprising an aqueous medium containing a biocidally effective amount of a hydantoin fatty acid ester of the formula

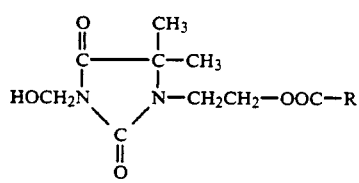

wherein R—COO— is a fatty acid moiety and wherein the fatty acid moiety has 8 to 18 carbon atoms.

2. The composition of claim 1 wherein the fatty acid moiety is an acetic, caprylic, capric, lauric, coconut, oleic, isostearic or stearic moiety.

3. The composition of claim 1 in the form of a mixture of esters of different fatty acid moieties.

4. The composition of claim 1 wherein the ester is a mixture of the 2-(3-hydroxymethyl-5,5-dimethyl-1,3-diazacyclopentane-2,4-diol-1-yl)-ethyl esters of caprylic acid and capric acid.

5. The composition of claim 1 wherein the ester is the 2-(3-hydroxymethyl-5,5-dimethyl-1,3-diazacyclopentane-2,4-dion-1-yl)-ethyl ester of lauric acid.

6. The composition of claim 1 wherein the ester is the 2-(3-hydroxymethyl-5,5-dimethyl-1,3-diazacyclopentane-2,4-dion-1-yl)-ethyl ester of coconut fatty acid.

7. The composition of claim 1 wherein the ester is the 2-(3-hydroxymethyl-5,5-dimethyl-1,3-diazacyclopentane-2,4-dion-1-yl)-ethyl ester of oleic acid.

8. The composition of claim 1 wherein the ester is the 2-(3-hydroxymethyl-5,5-dimethyl-1,3-diazacyclopentane-2,4-dion-1-yl)-ethyl ester of isostearic acid.

9. The composition of claim 1 wherein the ester is the 2-(3-hydroxymethyl-5,5-dimethyl-1,3-diazacyclopentane-2,4-dion-1-yl)-ethyl ester of stearic acid.

10. Composition of claim 1 wherein said ester is present in an amount of about 0.1–10% by weight of the total composition.

* * * * *